United States Patent [19]

Saletan

[11] Patent Number: 4,900,849
[45] Date of Patent: Feb. 13, 1990

[54] PROCESS FOR THE PRODUCTION OF DICHLOROHYDRIN

[75] Inventor: David I. Saletan, Houston, Tex.

[73] Assignee: Shell Oil Company, Houston, Tex.

[21] Appl. No.: 242,945

[22] Filed: Sep. 9, 1988

[51] Int. Cl.[4] .................... C07D 301/24; C07C 29/66
[52] U.S. Cl. .................................... 549/521; 568/847
[58] Field of Search ........................ 568/847; 549/521

[56] References Cited

U.S. PATENT DOCUMENTS 2,062,002 11/1936 Groll et al. ........................... 568/847
2,902,519 9/1959 Cosby et al. ......................... 568/847

FOREIGN PATENT DOCUMENTS 661112 4/1963 Canada ................................. 549/521

Primary Examiner—Howard T. Mars
Attorney, Agent, or Firm—Ronald R. Reper

[57] ABSTRACT

A process for the continuous production of di- and/or epichlorohydrin is disclosed wherein impurities, e.g., chloroaliphatic alkanes and chloroaliphatic ethers are removed by energy efficient solvent extraction and are obtained in relatively concentrated form for further processing or disposal.

7 Claims, 1 Drawing Sheet

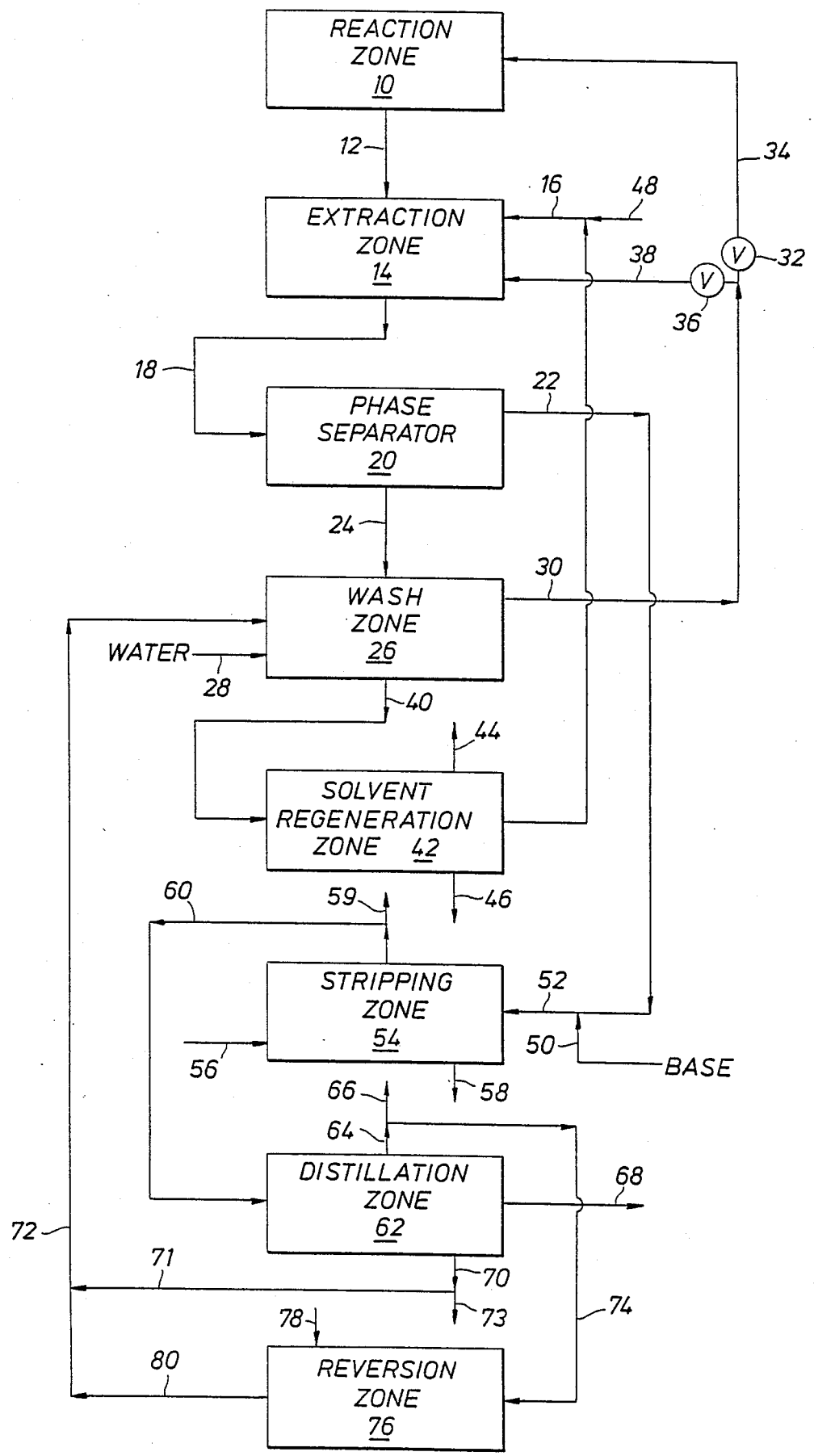

PROCESS FOR THE PRODUCTION OF DICHLOROHYDRIN

BACKGROUND OF THE INVENTION

This invention relates to an improved process for reacting allyl chloride, water and chlorine to produce dichlorohydrin. "Dichlorohydrin" is a term employed herein to designate the isomers 1,2-dichloro-3-hydroxypropane and 1,3-dichloro-2-hydroxypropane.

It is known to prepare an aqueous solution of dichlorohydrin by reacting in a reaction zone allyl chloride, water and chlorine in a dilute aqueous phase. U.S. Pat. No. 2,714,121, incorporated herein by reference, discloses producing halohydrins by using high dilution of, e.g., 250–400 volumes of water per volume of, e.g., a halosubstituted hydrocarbon in aqueous medium with subsequent addition of the halogen, and keeping the organic by-product phase dispersed as fine particles. U.S. Pat. No 2,714,123, incorporated herein by reference, discloses producing an aqueous solution of dichlorohydrin in a series of reaction stages wherein substantially all of the water is fed to the first reaction stage and the other reactants are added in substantially equimolar proportions into each of the subsequent reaction stages.

The reaction zone effluent may be worked up in various ways to recover the dichlorohydrin therefrom, or may be processed further in an integrated process to convert the dichlorohydrin to derivatives such as epichlorohydrin and/or glycerine.

It is known, e. g., from Belgian Pat. Nos. 614,890 and 614,891 that dichlorohydrin may be extracted from aqueous solution with organic solvents such as phosphate esters of aliphatic monohydric alcohols containing more than four carbon atoms, aryl phosphates, and liquid aliphatic alcohols and liquid ketones having 8 to 18 carbon atoms per molecule. U.S. Pat Nos. 4,620,911 and 4,665,240 disclose as further solvents for dichlorohydrin saturated aliphatic ethers and chlorinated hydrocarbons containing up to about 9 carbon atoms, including, e.g., carbon tetrachloride. The aforesaid U.S. Pat. Nos. 4,620,911 and 4,665,240 employ solvent extraction together with membrane processes to reduce the amount of fresh water fed to the reaction zone of the process.

One disadvantage of the known processes is the formation of undesired by-products, which reduce the overall efficiency of the process and may complicate purification procedures of the desired product. Such conventional processes result in an aqueous effluent stream which contains minor amounts of organic impurities diluted in a substantial amount of water. Such effluent requires energy intensive treatment to reduce the amount of organic materials to levels acceptable to be passed to receiving bodies of water such as rivers, lakes and the like. Considerable savings could be effected if the amount of organics to be treated could be significantly reduced.

A further disadvantage of the known processes is that polychlorinated alkane byproducts are formed during the aqueous dichlorohydrin synthesis. When, as is often the case, it is desired to further convert the dichlorohydrin to epichlorohydrin (1,2-epoxy-3-chloro-propane) in a subsequent step by the action of basic reagents, said byproducts are dehydrochlorinated to form chloroaliphatic impurities which have volatility close to epichlorohydrin. These impurities, although removable by conventional fractional distillation procedures, require inordinate input of energy to achieve epichlorohydrin purity required for a number of demanding end-use applications. The present invention advantageously substantially removes the precursor impurities from the dichlorohydrin prior to conversion to epichlorohydrin and in a manner which is much more energy efficient than finishing of epichlorohydrin by conventional distillation.

A method has now been found to reduce the level of chloraliphatic alkanes and chloraliphatic ethers impurities in the dichlorohydrin product and to obtain said impurities in relatively concentrated form for further processing or disposal.

SUMMARY OF THE INVENTION

According to the invention there is provided in a continuous process for the production of dichlorohydrin, the method for reducing the level of impurities selected from the group of chloroaliphatic alkanes and chloroaliphatic ethers, which method comprises:

(a) reacting allyl chloride, water and chlorine in a reaction zone to form an aqueous mixture of dichlorohydrin, together with minor amounts of impurities selected from the group of chloroaliphatic alkanes and chloroaliphatic ethers;

(b) contacting in an extraction zone said reaction zone effluent with less than about 8% by volume of a water-immiscible solvent for said impurities having a greater selectivity for said impurities than for dichlorohydrin, and an atmospheric boiling point from about 40° C. to about 105° C. to obtain as extract an impurity-enriched solvent, and an aqueous phase containing a major amount of the dichlorohydrin;

(c) separating said extract from said aqueous phase;

(d) contacting in a water wash zone said separated extract from step (c) with water to obtain a water wash stream containing a major portion of dichlorohydrin present in the feed to step (d), and a washed extract stream containing less dichlorohydrin than said feed to step (d);

(e) recycling said water wash stream to at least one of step (a) and step (b);

(f) passing said washed extract stream from step (d) as feed to a distillation zone, and fractionating said feed by fractionation distillation to obtain an overhead stream containing impurities boiling at a temperature lower than the boiling temperature of said solvent, a residual fraction containing impurities boiling at a temperature higher than the boiling temperature of said solvent, and an intermediate stream comprising regenerated solvent containing fewer impurities than said feed; and (g) recycling said regenerated solvent to step (b).

BRIEF DESCRIPTION OF THE DRAWING

The drawing depicts a schematic flow diagram of a preferred embodiment of the invention.

DESCRIPTION OF PREFERRED EMBODIMENTS

In the principal reaction, allyl chloride is converted to a mixture of the two isomers of glycerol dichlorohydrin by reaction with hypochlorous acid, HClO which is readily formed when chlorine is dissolved in water. The chlorohydrination reaction takes place readily at temperatures in the range from about 15° C. to about 75° C. The reaction typically results in the formation of undesired by-products such as, e.g., trichloropropane and tetrachloropropyl ether; such by-product formation may be aggravated by, e.g., the presence of allyl chloride in excess of its aqueous solubility. For maximum dichlorohydrin yield it is necessary to run the reaction at low concentrations of chloride ion and of chlorohydrin, i.e., with high water dilution. However, high water dilution may greatly increase the volume of aqueous effluent from the process which must be treated to remove tetrachlorpropyl ethers and other by-products.

The chloroaliphatic alkane and chloroaliphatic ether impurities are extracted from the reaction zone effluent into a small amount of solvent having greater solvency at the extraction temperature for said impurities than for the dichlorohydrin. Inert organic solvents suitably employed to effectively remove said impurities from the aqueous glycerol dichlorhydrin solution include polyhalo-aliphatic and aliphatic hydrocarbons having an atmospheric boiling point from about 40° C. to about 105° C. and which are resistant to decomposition by a strong base such as slaked lime in aqueous solution at a temperature of 100° C. A preferred solvent is carbon tetrachloride. Additional solvents include methylene chloride, methylene bromide, 1,1- dichloroethane, 1,1 dichloropropane, cyclohexane, and n-heptane. Particularly preferred are solvents having a density difference from water (either more dense or less dense than water) of at least 0.1 g/ml, and particularly a density difference of at least 0.25 g/ml when measured at a temperature of 50° C. This density difference facilitates ready separation of the solvent from the aqueous phase.

The extraction is carried out using conventional extraction techniques, wherein the impurities are extracted into the solvent. The solvent is then separated from the remaining aqueous phase, following which the solvent may be regenerated as described hereinbelow, and recycled to the extraction zone.

An illustrative embodiment of the invention will now be described with reference to the accompanying drawing which shows schematically a preferred assemblage adapted to the continuous manufacture of dichlorohydrin. The reaction zone may comprise one or more reaction stages in parallel or consecutive flow, comprised of stirred reactors, circulating loop reactors, vane disc turbine dispersers, sprayed towers or other equipment known to be suitable for chlorohydrin reactions.

Referring to the drawing, effluent from the reaction zone 10 is passed via conduit 12 to extraction zone 14 which may be any conventional liquid-liquid extractor such as an agitated vessel, jet mixer, perforated plate tower, rotating disc contactor and the like. Preferred for its simplicity and ease of operation is an injection line 16 providing solvent just upstream of an orifice plate (not shown) to ensure good contacting of the solvent with the reaction zone effluent. Although counter current extraction may be used, cocurrent flow with a very minor amount of solvent is suitable. Generally the amount of solvent contacted with the aqueous phase should be in a solvent to aqueous phase volume ratio of from about 1:100 to about 8:100, with a volume ratio of 1.5:100 to about 4.5:100 being preferred. Generally when cocurrent flow is employed it will be desirable to separate the mixture of aqueous phase and extraction solvent into the respective phases. As shown in the drawing the mixed phases are passed from extraction zone 14 via conduit 18 to phase separator 20 which may be any conventional phase separator such as a centrifugal separator, hydroclone and the like. The aqueous phase containing a major amount of the dichlorohydrin and a significantly smaller amount of the chloroether and chloroaliphatic alkane impurities is removed from phase separator 20 via conduit 22 for concentration, or for chemical conversion into derivatives such as epichlorohydrin or glycerine.

The impurities-fat solvent, also referred to herein as separated extract, is passed from the separation zone 20 via conduit 24 to water wash zone 26. In water wash zone 26, which may comprise one or more separate stages the impurities-fat solvent is contacted with water supplied via conduit 28 to remove a substantial portion of any dichlorohydrin product that may be contained therein resulting in a washed extract stream and a water wash stream containing a major portion of dichlorohydrin present in the stream(s) fed to water wash zone 26. In a preferred mode the water wash stream removed from said wash zone 26 is recycled via conduit 30, valve 32 and conduit 34 to the reaction zone 10 and may displace a like amount of fresh water ordinarily supplied to said reaction zone. Alternately, the water from wash zone 20 may be recycled to extraction zone 14 via conduit 30 valve 36 and conduit 38. Preferably the amount of water contacting the impurities-fat solvent in the washing zone is in a water to solvent volume ratio from about 4:1 to about 8:1 although greater or smaller amounts may be used.

From wash zone 26 the washed extract stream is passed via conduit 40 to solvent regeneration zone 42 for regeneration by fractional distillation. Both the chloroether and polychloroaliphatic (such as 1,2,3,-trichloropropane) impurities will be less volatile than the solvent chosen, which can therefore be removed as an overhead fraction via conduit 44, leaving both classes of impurities as a bottom residual fraction which can be removed via conduit 46 for further use or disposal. Typically there will also be monochloroaliphatic impurities arising from side reactions of the allyl chloride starting material and possibly some impurities, such as monochloropropanes, introduced with the allyl chloride charged to reaction zone 10. These lighter impurities have boiling points lower than the preferred solvents, such as carbon tetrachloride, employable in this process. Accordingly in a preferred embodiment the regenerated solvent is recovered as an intermediate fraction via conduit 16.

In order to compensate for minor solvent losses through the process, a small amount of solvent may be added via conduit 48 along with the recycle solvent to maintain the desired ratio of solvent to reaction zone effluent.

A preferred embodiment according to the invention further provides an integrated process wherein the aqueous dichlorohydrin product from phase separator 20 is converted to epichlorohydrin as shown in the lower part of the drawing and any solvent remaining in said aqueous phase is recovered and reused.

The aqueous dichlorohydrin phase from separator 20 is withdrawn via conduit 22, contacted with a aqueous base such as, e.g., slaked lime, sodium hydroxide or sodium carbonate supplied via conduit 50 to convert the dichlorohydrin to epichlorohydrin which is immediately stripped from the aqueous solution in stripping zone 54 with steam supplied via conduit 56. The stripped aqueous phase exits stripping zone 54 via conduit 58 for further treatment and disposal. The liquid resulting from condensed overhead vapor from stripping zone 54 forms two layers. The upper layer comprising substantially water with a small amount of epichlorohydrin is returned to a rectifying section in the top of stripping zone 54 as reflux. The lower layer comprising primarily epichlorohydrin together with a small amount of steam condensate is passed as an overhead stream via conduit 60 to distillation zone 62 for purification of the epichlorohydrin by fractional distillation. A small gaseous vent stream 59, consisting essentially of fixed gases such as nitrogen which entered the system with the reactants fed to the reaction zone 10, together with some low boiling organic compounds such as acrolein, which may be generated in stripping zone 54 from by-products formed in the reaction zone 10 is removed for further treatment or disposal, such as combustive disposal in a conventional flare system.

Distillation zone 62 may comprise one column, but preferably is two or a plurality of columns (not shown) arranged to separate water, solvent and other lower boiling materials as an overhead fraction withdrawn via conduits 64 and 66, the desired epichlorohydrin as a very pure intermediate fraction withdrawn via conduit 68, and residual high-boiling impurities as a bottoms fraction, withdrawn via conduit 70. Said bottoms fraction in conduit 70 comprises primarily 1,2 dichlorohydrin which failed to react completely in stripping zone 54 together with small amounts of the chloroethers and trichloropropane which were not extracted in extraction zone 14. In a preferred embodiment most of the bottoms fraction in conduit 70 is recycled via conduits 71 and 72 to water wash zone 26 for recovery of the dichlorohydrin content, with small continuous or intermittent purge of said bottoms fraction via conduit 73 to waste, e.g., incineration. The purge is to prevent or control possible build-up in the system of the undesirable trace isomeric impurity of epichlorohydrin, 2-chloro-allyl alcohol.

The overhead fraction in conduit 64 is partially condensed to recover any solvent and or epichlorohydrin therein, with the uncondensed vapors passing to waste, e.g., combustive disposal via conduit 66 (similar to the disposal of gases via conduit 59). The condensed portion is passed via conduit 74 to reversion zone 76 for contact with chloride ion to convert any epichlorohydrin that may be present back to dichlorohydrin. Reversion zone 76 which may be any liquid-liquid contactor, is preferably a stirred vessel where the condensate may be contacted with, e.g., hydrochloric acid, added via conduit 78. Although any chloride ion source could be employed in the reversion step, hydrochloric acid is most preferred as it is already present in the manufacturing process for dichlorohydrin and the acidity improves both the rate and selectivity to the desired dichlorohydrin. An aqueous system should be used in the reversion zone to prevent polymerization reaction which could form undesired high molecular weight polyols. Although hydrochloric acid is in principle already available in conduit 12 for the reversion reaction, use of a separate reversion zone enables better control and more selective reversion of epichlorohydrin back to dichlorohydrin. From reversion zone 76, the reverted condensate is recycled via conduits 80 and 72 to wash zone 26 for recovery of the solvent and dichlorohydrin. In this preferred embodiment the epichlorohydrin is reverted back to the more water soluble dichlorohydrin before recycle of the stream to avoid contaminating the impurities-fat solvent in conduit 24 with epichlorohydrin. For some applications, e.g., where more than one stage is employed in the water wash zone, it may be desirable to convey the reversion zone product via a conduit (not shown) separate from the conduit carrying the bottoms fraction from the distillation zone to said water wash zone to enable contacting of the reversion zone product in a different stage of said water wash zone than is applied for contacting of said bottoms fraction with water in said water wash zone.

What is claimed is:

1. In a continuous process for the production of dichlorohydrin an improvement for reducing the level of chloroaliphatic alkanes and chloroaliphatic ethers impurities in the dichlorohydrin product the improvement comprising in sequence:
    (a) reacting allyl chloride, water and chlorine in a reaction zone to form an aqueous mixture of dichlorohydrin, together with minor amounts of chloroaliphatic ethers impurities;
    (b) contacting in an extraction zone said reaction zone effluent with less than about 8% by volume of a water-immiscible solvent for said impurities having a greater solvency for said impurities than for dichlorohydrin and an atmospheric boiling point from about 40° to about 105° C., to obtain as extract an impurity-enriched solvent, and an aqueous phase containing a major amount of the dichlorohydrin;
    (c) separating said extract from said aqueous phase;
    (d) contacting in a water wash zone said separated extract from step (c) with water to obtain a water wash stream containing a major portion of dichlorohydrin present in the feed to step (d), and a washed extract stream containing less dichlorohydrin than said feed to step (d);
    (e) recycling said water wash stream to at least one of step (a) and step (b);
    (f) passing said washed extract stream from step (d) as feed to a distillation zone, and fractionating said feed by fractional distillation to obtain an overhead stream containing impurities boiling at a temperature lower than the boiling temperature of said solvent, a residual fraction containing impurities boiling at a temperature higher than the boiling temperature of said solvent, and an intermediate steam comprising regenerated solvent containing fewer impurities than said feed; and
    (g) recycling said regenerated solvent to the extraction zone of step (b).

2. A process as in claim 1, wherein said solvent is carbon tetrachloride.

3. A process as in claim 1 comprising the further steps of
    (h) contacting said aqueous phase from step (b) with a basic substance to obtain a basic aqueous phase and substantially simultaneously stream stripping said basic aqueous phase to convert said dichlorohydrin to epichlorohydrin;
    (i) fractionating said epichlorohydrin by fractional distillation to obtain an overhead fraction containing any solvent which had been entrained in said aqueous phase from step (b);
    (j) contacting said overhead fraction with a source of chloride ion in aqueous solution to revert any epichlorohydrin therein to dichlorohydrin resulting in a reverted overhead fraction; and
    (k) recycling said reverted overhead fraction to at least one of step (a), step (b), step (c) or said step (d).

4. A process as in claim 3 wherein step (k) said reverted fraction is recycled to the water wash zone of step (d).

5. A process as in claim 1 wherein at least a portion of the water wash stream removed from the water wash zone is recycled to the reaction zone.

6. A process as in claim 1 wherein step (d) said separated extract is contacted with water in a water to solvent volume ratio from about 4:1 to about 8:1.

7. A process as in claim 1 wherein at least part of the residual fraction obtained in step (f) is recycled to the water wash zone of step (d).

* * * * *